United States Patent [19]

Mitchell

[11] 3,976,589

[45] Aug. 24, 1976

[54] METHODS OF SCALE INHIBITION

[75] Inventor: Robert S. Mitchell, Webster Groves, Mo.

[73] Assignee: Monsanto Company, St. Louis, Mo.

[22] Filed: Dec. 16, 1974

[21] Appl. No.: 533,037

Related U.S. Application Data

[63] Continuation-in-part of Ser. No. 169,050, Aug. 4, 1971, abandoned.

[52] U.S. Cl. .............................. 252/180; 252/181; 260/502.5
[51] Int. Cl.² ...................... C02B 5/00; C02B 5/04
[58] Field of Search ..................................... 252/181

[56] References Cited
UNITED STATES PATENTS

| | | | |
|---|---|---|---|
| 2,964,549 | 12/1960 | Ramsey............................... | 252/180 |
| 3,288,846 | 11/1966 | Irani et al. ................... | 260/502.5 X |
| 3,298,956 | 1/1967 | Irani et al. ................... | 260/502.5 X |

Primary Examiner—Mayer Weinblatt
Assistant Examiner—Edith R. Buffalow
Attorney, Agent, or Firm—Thomas B. Leslie

[57] ABSTRACT

The precipitation of scale-forming salt in an aqueous system is inhibited by adding either stoichiometric or substoichiometric amounts to said system of a substituted tertiary amine of the general formula

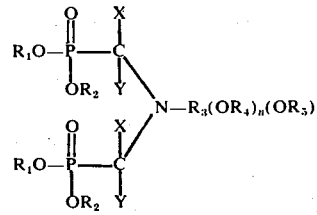

wherein $R_1$, $R_2$, $R_3$, $R_4$, $R_5$, X and Y are hereinafter defined and $n$ is 1–20.

8 Claims, No Drawings

METHODS OF SCALE INHIBITION

This application is a continuation-in-part of copending application Ser. No. 169,050, filed Aug. 4, 1971 now abandoned.

This invention relates to methods for inhibiting the precipitation of metal ions from aqueous solutions, and more particularly, to the use of certain substituted tertiary amines to accomplish this purpose.

Most commercial water contains iron and alkaline earth metal cations, such as calcium, barium, magnesium, etc., and several anions such as hydroxide, bicarbonate, carbonate, sulfate, oxalate, phosphate, silicate, fluoride, etc. When combinations of these anions and cations are present in concentrations which exceed the solubility of their reaction products under the conditions of the application (i.e., use), precipitates form until their reaction solubility product concentrations are no longer exceeded. For example, when the concentrations of calcium ion and sulfate ion exceed the solubility of the calcium sulfate, a solid phase of calcium sulfate will form.

Solubility product concentrations are exceeded for various reasons, such as evaporation of the water phase, change in pH, pressure or temperature, and the introduction of additional ions which form insoluble compounds with the ions already present in the solution.

As these reaction products precipitate on the surfaces of the water carrying system, they form scale. The scale prevents effective heat transfer, interferes with fluid flow, facilitates corrosive processes, and harbors bacteria. The presence of this scale is an expensive problem in many industrial water systems (e.g., boilers, cooling towers, evaporators, etc.), oilwells, and the like, causing delays and shutdowns for cleaning and removal.

Scale-forming compounds can be prevented from precipitating by inactivating their cations with chelating or sequestering agents, so that the solubility of their reaction products is not exceeded. Generally, this requires many times as much chelating or sequestering agent as cation, and these amounts under certain conditions are not always desirable or economical.

More than 25 years ago it was discovered that certain inorganic polyphosphates would prevent such precipitation when added in amounts less than the concentrations needed for sequestering or chelating. See, for example, Hatch and Rice, "Industrial Engineering Chemistry," vol. 31, pages 51 and 53; Reitmeier and Buehrer, "Journal of Physical Chemistry," vol. 44, No. 5, pages 535 and 536 (May 1940); Fink and Richardson U.S. Pat. No. 2,358,222; and Hatch U.S. Pat. No. 2,539,305, all of which are incorporated herein by reference. For sequestration, the mole ratio of precipitation inhibitor equivalents to scale forming cation is usually 1:1 or greater (2:1, 3:1, etc.). These ratios are referred to as stoichiometric. Substoichiometric amounts would include all mole ratios of precipitation inhibitor equivalent to scale forming cation that are less than the level required for sequestration; this phenomenon is known in the water treating art as the "threshold" effect.

It is to be understood that the term "threshold" as utilized herein refers to the chemical and/or physical phenomenon that less than stoichiometric quantities of the particular precipitation inhibitor can effectively prevent the precipitation of various metallic ions such as calcium, iron, copper and cobalt and/or alter those crystals formed such that the adherence to surfaces is substantially reduced. In other words, the "threshold" treatment of water is that technique by means of which less than stoichiometric quantities of the treating agent are added to interfere with the growth of crystal nuclei and thereby prevent the deposition of insoluble deposits.

Consequently, precipitation inhibitors which function as a threshold agent and a sequestering agent represent an advancement in the art and are in substantial demand.

Therefore, an object of this invention is to provide a method for inhibiting the precipitation of metal ions from aqueous solutions.

Another object of this invention is to provide a precipitation inhibitor which is effective in inhibiting the precipitation of metal ions in acid or alkaline aqueous solutions.

A still further object of this invention is to provide a precipitation inhibitor which is effective in inhibiting the precipitation of iron ions and calcium ions in acid or alkaline solutions.

Other objects will become apparent from a reading of the following detailed description.

It has been found that certain substituted tertiary amines corresponding to the following formula

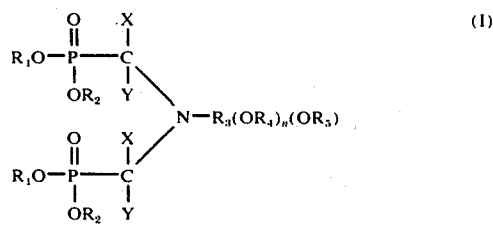

unexpectedly function as superior precipitation inhibitors when used in substoichiometric concentrations. The phenomenon includes what is generally known in the art as the "threshold effect". Furthermore, these substituted tertiary amine compounds function as sequestering agents where one so desires to use the same.

In Formula I above, $R_1$ and $R_2$ can be alike or unlike and are from the group metal ions and hydrogen or any cation which will yield sufficient solubility for the desired end-use. The aforementioned metal ions are from the group of metals which includes, without limitation, alkali metals such as sodium, lithium and potassium; alkaline earth metals, such as calcium and magnesium; aluminum; zinc, cadmium; manganese; nickel, cobalt, cerium; lead; tin; iron; chromium; copper; gold; and mercury. Also included are ammonium ions and alkyl ammonium ions. In particular, those alkyl ammonium ions derived from amines having a low molecular weight, such as below about 300, and more particularly the alkyl amines, alkylene amines, and alkanol amines containing not more than two amine groups, such as ethyl amine, diethyl amine, propyl amine, propylene diamine, hexyl amine, 2-ethylhexylamine, N-butylethanol amine, triethanol amine, and the like are the preferred amines. It is to be understood that the preferred metal ions are those which render the compound a water-soluble salt in concentrations sufficient for the desired applications, such as the alkali metals, as well as the water-soluble salts from ammonium, alkyl ammonium and alkanol amine ions.

In Formula I above, $R_3$ is an alkylene group containing from 3 to 5 carbon atoms, such as propylene, butylene and the like. It is preferred that $R_3$ be a propylene group. $R_4$ is an alkylene group containing from 2 to 5 carbon atoms, preferably an ethylene group.

$R_5$ is an alkyl group containing from 1 to 5 carbon atoms; the preferred alkyl group is ethyl.

In Formula I above, X and Y are each alike or unlike and are from the group hydrogen and organic radicals such as alkyl containing less than 40, preferably 1 to 4 carbon atoms such as methyl, ethyl, propyl and the like. It is to be understood that organic radicals such as other aliphatic groups and also aromatic groups are included herein.

In Formula I, $n$ has a value of from 1 through 20. It is to be understood that all of the compounds falling within the above Formula I and as heretofore defined are generically described herein as "substituted tertiary amines" or "STA". In other words, then, the acids, salts and physical and chemical mixtures thereof are all generically described herein as "STA".

Illustrative (but without limitation) of some of the present invention STA are shown below:

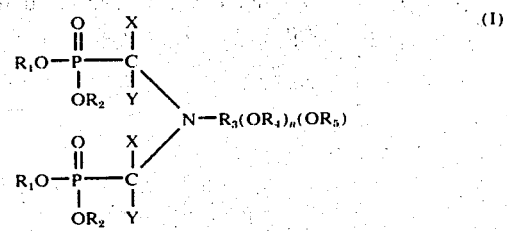

| Compound Number | $R_1$ | $R_2$ | $R_3$ | $R_4$ | $R_5$ | X | Y | n |
|---|---|---|---|---|---|---|---|---|
| 1 | H | H | $(CH_2)_3$ | $C_2H_4$ | $C_2H_5$ | H | H | 2 |
| 2 | " | " | " | " | " | " | " | 5 |
| 3 | " | " | " | " | " | " | " | 10 |
| 4 | " | " | " | " | " | " | " | 15 |
| 5 | " | " | " | " | " | " | " | 20 |
| 6 | " | " | " | " | " | $CH_3$ | $CH_3$ | 2 |
| 7 | " | " | $(CH_2)_4$ | " | " | H | H | 2 |
| 8 | " | " | $(CH_2)_5$ | " | " | " | " | 2 |
| 9 | " | " | $(CH_2)_3$ | $C_3H_6$ | " | " | " | 5 |
| 10 | " | " | " | " | " | " | " | 15 |
| 11 | " | " | $(CH_2)_5$ | $C_4H_8$ | $C_3H_7$ | " | " | 2 |
| 12 | —Zn— | | $(CH_2)_3$ | $C_2H_4$ | $C_2H_5$ | " | " | 2 |
| 13 | Na | Na | " | " | " | $CH_3$ | $CH_3$ | 2 |
| 14 | H | H | " | " | " | H | H | 1 |
| 15 | Na | Na | " | " | " | " | " | 8 |
| 16 | H | H | " | " | $CH_3$ | " | " | 2 |
| 17 | Na | Na | " | " | $C_2H_5$ | " | " | 2 |

The STA falling within the aforegoing Formula I are prepared according to my copending patent applications Ser. No. 169,131, filed Aug. 4, 1971 and a continuation-in-part thereof filed concurrently herewith and which are incorporated herein by reference.

The precipitation inhibitors, i.e., STA, of the present invention have utility whenever it is desired to inhibit the precipitation of metal ions from aqueous solutions (and/or alter those crystals formed such that the adherence to surfaces is substantially reduced). Typical applications also include liquid soaps and shampoos (e.g., note U.S. Pat. No. 3,313,735); bar soaps; scouring wool cloth; cotton kier boiling; cotton dyeing; cotton bleaching; metal cleaning compounds; rubber and plastics trace metal contamination (compounding and polymerization); pulp and paper trace metal contamination; saline water (e.g., note U.S. Pat. No. 3,505,238); oral composition as anticalculus agents (e.g., note U.S. Pat. Nos. 3,488,419, 3,535,420 and 3,535,421); photographic developers (e.g., note U.S. Pat. No. 3,201,246); hair bleaching and dyeing operations (e.g., note U.S. Pat. No. 3,202,579); stabilizing hydrogen peroxide solutions (e.g., note U.S. Pat. Nos. 3,383,174 and 3,234,140); brine solutions (e.g., note U.S. Pat. No. 3,385,675); brackish water; and squeeze treatment of producing oil wells (e.g., note U.S. Pat. No. 3,483,925). All of the above patents are incorporated herein by reference.

The amount of the precipitation inhibitor necessary to be effective varies with, inter alia, the type and amount of problem metal ions, pH conditions, temperature and the like. When using substoichiometric amounts, the preferred mole ratio of the precipitation inhibitor to the scale forming cation salt is from about 1:1.5 to about 1:10,000. When using sequestering amounts, i.e., at least stoichiometric quantities, the preferred mole ratio is from about 1:1 to 2.5:1.

It is within the scope of the present invention that the precipitation inhibitors of the present invention may also be used in aqueous systems which contain inorganic and/or organic materials (particularly, all ingredients or substances used by the water-treating industry), with the proviso that such materials do not render the precipitation inhibitors substantially ineffective for their end purpose.

These organic and inorganic materials include those ingredients or compositions described and disclosed in the United States patents heretofore set forth. Such materials also include, without limitation, polycarboxylates, particularly those whose molecular weights are from about 2000 to about 20,000 (e.g., note U.S. Pat. No. 3,514,376 which is incorporated herein by reference) and from about 20,000 to about 960,000 (e.g., note U.S. Pat. No. 3,293,150 which is incorporated herein by reference); antifoam agents; water soluble polymers; tannins; lignins; deaerating materials; polymeric anhydrides (such as polymaleic anhydride); and sulfonated lignins. In addition, water-soluble inorganic chromates such as those described in U.S. Pat. No. 3,431,217 (which is incorporated herein by reference) may be used in combination with said inhibitors. Other materials which can be used with said precipitation inhibitors include, for example, surface active agents and corrosion inhibitors such as (1) those described in *Corrosion Inhibitors*, by Beegman, published by Mac-Millan in 1963; U.S. Pat. No. 3,483,153 and 3,532,639, all of which are incorporated herein by reference and (2) inorganic silicates. Furthermore, other precipitation inhibitors such as amino tri(methylene phosphonic acid) may be used in combination with the precipitation inhibitors of the present invention. For exemplary purposes only, these other precipitation inhibitors are described in U.S. Pat. Nos. 2,970,959; 3,234,124; 3,336,221; 3,393,150; 3,400,078; 3,400,148; 3,434,969; 3,451,939 and 3,462,365, all of which publications are incorporated herein by reference.

The following examples are included to illustrate the practice of the present invention and the advantages provided thereby but are not to be considered limiting. Unless otherwise specified, all parts are parts by weight and all temperatures are in degrees centigrade.

EXAMPLE I

In order to demonstrate the sequestering ability of the STA falling within Formula I above, the compounds identified above as Nos. 1 through 17 are subjected to the sequestration procedure described in the book COORDINATION CHEMISTRY, "Calcium Complexing By Phosphorus Compounds", by C. F. Callis, A. F. Kerst and J. W. Lyons, pages 223–240, Plenum Press, 1969.

Approximately 1 gram of each of the above described compounds (STA "sequestration agents") is individually and separately mixed with 0.1% by weight sodium oxalate in a 2-liter flask containing 1000 milliliters of water. The pH in each case is adjusted by the addition of sodium hydroxide to a pH 11. Into each solution containing the separate and individual sequestration agents there is titrated a 0.1 molar calcium nitrate solution via the use of a Sargent-Malmstadt automatic titrator, Model SE, and which also measures the turbidity by light transmission. The amount of calcium nitrate solution added to each flask is sufficient to provide ample data to plot the point of inflection at which the sequestrant-containing solution goes from a relatively clear solution to a turbid one. This inflection point is then indicative of the amount of calcium that is sequestered by the particular sequestration agent.

The results of the sequestration test on compounds Nos. 1 through 17 show that the various STA are good sequestrants for calcium which is one of the major undesirable cations in water which is used, for example, in cooling towers. Specifically, it is found that 100 grams of the STA—compound No. 1—sequesters approximately 1.6 grams of calcium. It is also found that the other STA (compounds 2 through 17) sequester calcium in a range of from about 0.3 grams to about 4.8 grams of calcium per 100 grams of the STA.

EXAMPLE II

The following example is carried out illustrating the iron sequestering ability of the STA.

The testing procedure consists of pipetting an aliquot volume of 2.5% ferric chloride solution into a beaker and adding thereto enough sodium hydroxide or hydrochloric acid to give the desired pH. The solution is stirred for fifteen minutes, followed by the addition of an aliquot of 2.5% of the sequestering agent solution, i.e., the particular STA (in the salt form where necessary) dissolved in water. After final pH adjustment with sodium hydroxide or hydrochloric acid, the solution is shaken for 48 hours to reach equilibrium. The solution is then centrifuged at about 12,000 rpm for approximately 55 minutes to remove colloidal ferric hydroxide and an aliquot of the supernatant solution is titrated iodometrically or analyzed by X-ray fluorescence with use of an appropriate calibration curve in order to determine the ferric iron concentration. The ferric iron concentrations and sequestering agent concentrations found in parts per million (ppm) are converted to a weight basis and expressed as pounds of iron sequestered by 100 pounds of sequestering agent.

Following the above described procedure, each of the compounds Nos. 1 through 17 heretofore described is individually tested. In each case it is found that the precipitation inhibitors of the instant invention demonstrate an unexpected and unique ability to sequester ferric iron over a wide range of pH conditions, i.e., from about 4 to about 10.5, and that the average amount (in pounds) of iron sequestered by 100 pounds of the respective precipitation inhibitor (compound No.) over the 4 to 10.5 pH range is in each case at least 3.5 pounds of iron (III).

EXAMPLE III

The above Example II is repeated several times with the exception that other metal ion-containing solutions such as calcium, copper, nickel and chromium are utilized in place of the ferric (chloride) solution. In each case utilizing the aforementioned compounds the average sequestration values of these latter mentioned ions respectively are found to be similar to those set forth above.

Example II is again repeated several times utilizing as a sequestering agent trisodium nitrilotriacetate .$2H_2O$, sodium citrate, and potassium gluconate. It is found that the pounds of iron sequestered by 100 pounds of the aforementioned sequestering agents respectively are 7.0, 6.5 and 2.9 over the same pH range of 4 to 10.5. It can readily be seen, then, that the STA (in the acid or salt forms) of the present invention when utilized as sequestering agents are equally as effective as the widely used organic sequestering agents under comparative conditions and in some cases are superior thereto. Furthermore, when such derivatives of the present invention are utilized as sequestering agents, they exhibit an effectiveness as such over a wide range of pH conditions. This is highly advantageous in permitting their respective use in many and varied applications.

EXAMPLE IV

The present invention STA falling within Formula I also exhibit threshold properties, i.e., they can be utilized in less than stoichiometric quantities to prevent the precipitation of salts of mineral acids, such as $CaCO_3$, in aqueous systems. Specifically, a test is conducted in which each of the compounds, i.e., Nos. 1 through 17, is separately and independently mixed at 25°C with 250 milliliters of water containing $CaCl_2$. To the resultant mixture is added $NaHCO_3$. The pH in each case is adjusted to 7 and maintained thereat with sufficient NaOH or HCl. The amounts of $CaCl_2$, $NaHCO_3$ and inhibiting agent used are sufficient to provide 5000 ppm of $CaCO_3$ and 10 ppm of the indicated STA (precipitation inhibitor). It is observed in each case that these less than stoichiometric quantities of said precipitation inhibitors (threshold agents) effect a substantially clear solution for a period of at least 48 hours. Stating the results in a different manner, 10 parts per million of the indicated STA (threshold agent) is effective in providing a clear solution without precipitation which contains substantially greater than stoichiometric quantities of calcium carbonate therein.

EXAMPLE V

The above Example IV is repeated several times with the concentration of the specific STA additive being respectively 25 ppm, 100 ppm, 200 ppm and 500 ppm. The results utilizing these different concentrations are similar to the results obtained in Example IV.

EXAMPLE VI

Two solutions, A and B, are prepared in order to demonstrate the "threshold effect" of only 5 parts of ethoxy, ethoxy, ethoxy propylamino di(methylene phosphonic acid)-(Compound No. 1) per 1,000,000 parts of solution containing large quantities of CaSO₄. (The 5 ppm is based on a 100% active phosphonic acid basis.) Solution A is prepared by dissolving the appropriate amount of said acid in water and then adding calcium chloride followed by the addition of sodium sulfate. The amounts of sodium sulfate and calcium chloride used are sufficient to result in the solution containing 10,000 ppm of CaSO₄ and then the pH is adjusted to 7. Solution B is prepared in the same manner except that the CaSO₄ concentration is 15,000 ppm. The solutions are stored with continuous agitation (NBS Gyrotory Shaker) at 25°C. Two "control" solutions C and D are prepared in the same manner as solutions A and B except that the "control solutions" do not contain any of the STA threshold agent — i.e., said phosphonic acid.

These tests show that the "control" solutions C (10,000 ppm CaSO₄) and D (15,000 ppm CaSO₄) within a few minutes after preparation each result in the precipitation of CaSO₄. However, in solutions A and B (both of which contain said phosphonic acid), the solutions per se remain clear over an extended period of at least 24 hours at the 10,000 ppm CaSO₄ level and at least 12 hours at the 15,000 ppm CaSO₄ level. At the end of the aforementioned 12 hour and 24 hour periods, the solutions A and B are substantially clear to visual observation and about 90–100% of all the CaSO₄ remains in solution as further determined by titration of a sample of each solution with a standard solution of ethylene diamine tetraacetic acid using an Eriochrome Black T indicator.

EXAMPLE VII

The above Example VI is repeated in the same manner except that the threshold agent used is Compound No. 9, in place of Compound No. 1. Substantially the same results are obtained in this Example VII as those obtained in Example VI.

EXAMPLE VIII

Example VI is repeated in the same manner except that 5 ppm of a substituted tertiary amine derived from ethanol amine and containing a terminal hydroxyl group, ethanol amino di(methylenephosphonic acid), is used in place of Compound No. 1. In this case precipitation of CaSO₄ results within 3 to 5 hours in both solutions containing 10,000 ppm and 15,000 ppm CaSO₄. The results obtained after a 24-hour period show only three percent more CaSO₄ in solution than in control solution C (38% compared to 36% when titrated as above) at the 10,000 ppm CaSO₄ level. Thus, it is seen that the ethanol amino di(methylenephosphonic acid) does not demonstrate a practical "threshold effect" at the test level when compared to Compound No. 1 of Example VI.

The foregoing examples have been described in the foregoing specification for the purpose of illustration and not limitation. Many other modifications and ramifications will naturally suggest themselves to those skilled in the art based on this disclosure. These are intended to be comprehended as within the scope of this invention.

What is claimed is:

1. A method of inhibiting the precipitation of scale-forming salts in an aqueous system comprising adding at least a precipitation inhibiting amount of a substituted tertiary amine having the general formula

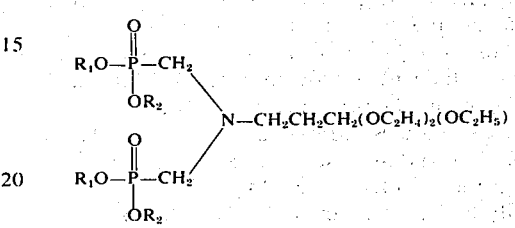

wherein R₁ and R₂ are alike or unlike and are each independently selected from the group consisting of alkali metal ions, hydrogen, and ammonium ions.

2. The method of claim 1 wherein the scale-forming salt is alkaline earth metal carbonates, sulfates, oxalates, phosphates, fluorides or silicates.

3. The method of claim 1 wherein the mole ratio of precipitation inhibitor to scale-forming salts is from about 1 to 1.5 to about 1 to 10,000.

4. The method of claim 3 wherein the precipitation inhibitor is present in the system at concentrations from about 0.1 part per million to about 500 parts per million.

5. The method as set forth in claim 1 wherein R₁ and R₂ are each an alkali metal ion.

6. The method as set forth in claim 1 wherein the substituted tertiary amine has the formula

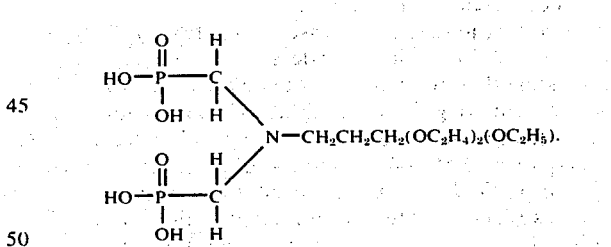

7. The method as set forth in claim 1 wherein the scale-forming salt is an iron hydroxide.

8. The method as set forth in claim 1 wherein the scale-forming salt is calcium sulfate.

* * * * *